United States Patent [19]

Doyle

[11] 4,098,157

[45] Jul. 4, 1978

[54] METHOD FOR SUTURE REMOVAL

[76] Inventor: Donald E. Doyle, 8147 Amor Rd., Los Angeles, Calif. 90046

[21] Appl. No.: 590,614

[22] Filed: Jun. 26, 1975

[51] Int. Cl.² .......................... B26D 3/00; B26D 11/00
[52] U.S. Cl. ........................................ 83/13; 128/305; 7/158
[58] Field of Search ............... 7/14.1 R, 1P; 30/329, 30/294, 165, 337, 317, 339, 315, 314; 81/43; 128/305, 354, 309; 83/13, DIG. 8

[56] References Cited

U.S. PATENT DOCUMENTS

| 219,633 | 9/1879 | Gifford | 81/43 |
|---|---|---|---|
| 2,597,564 | 5/1952 | Bugg | 30/DIG. 8 |
| 2,838,049 | 6/1958 | Eisenhofer et al. | 128/305 |
| 2,913,822 | 11/1959 | Wallbillich | 30/294 |
| 3,086,288 | 4/1963 | Balamuth et al. | 128/305 |
| 3,212,187 | 10/1965 | Benedict | 128/305 |
| 3,610,246 | 10/1971 | Salmon | 128/305 |
| 3,798,688 | 3/1974 | Wasson | 7/14.1 R |

OTHER PUBLICATIONS

Surgical Equipment, (Madison, Wisconsin), p. 10, vol. 2, No. 3, May–Jun. 1935.

*Primary Examiner*—James L. Jones, Jr.
*Assistant Examiner*—Roscoe V. Parker

[57] ABSTRACT

A method is provided for cutting and removing sutures with a thin, flat blade mounted on one end. The blade has a sharp, concave cutting edge and a flattened, convex bearing edge. The cutting and bearing edges converge to a sharp point at the first end of the blade and diverge towards a second end of the blade. The arc of the bearing edge is substantially equal to or less than the arc of the cutting edge. A handle is secured to the second blade end and an obtuse angle is formed between a line drawn parallel to the longitudinal axis of the handle and a line tangent to the bearing edge at the point. The blade cuts sutures as the sutures are lifted from the sutured surface by the blade being rotated away from the sutured surface and linearly advanced.

5 Claims, 7 Drawing Figures

U.S. Patent    July 4, 1978    4,098,157
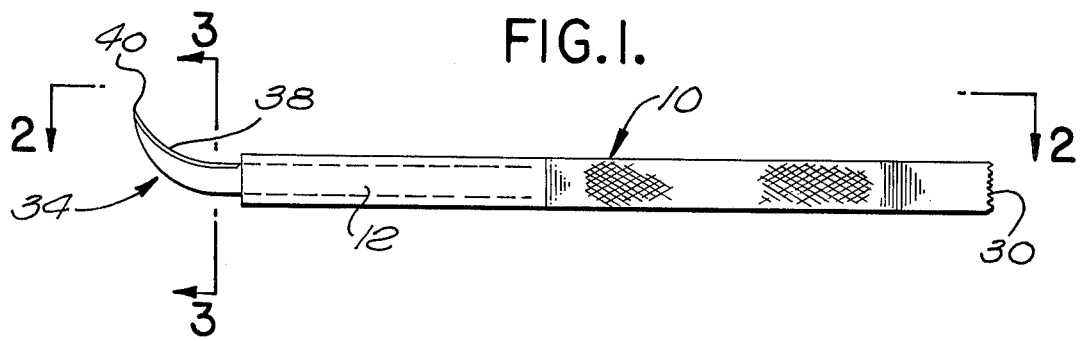
FIG. 1.
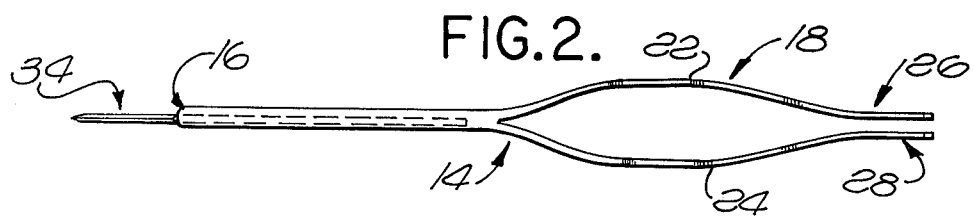
FIG. 2.
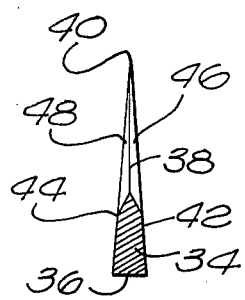
FIG. 3.
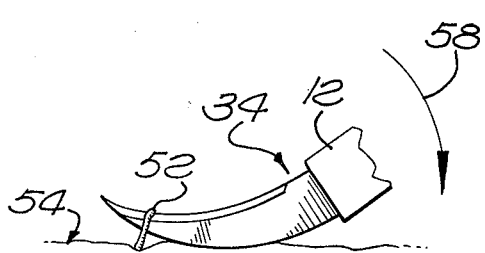
FIG. 4.
FIG. 5.
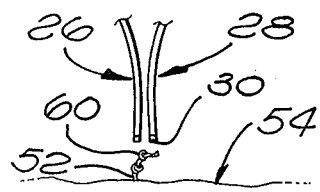
FIG. 6.
FIG. 7.

METHOD FOR SUTURE REMOVAL

BACKGROUND OF THE INVENTION

This invention relates to a method for cutting and removing sutures, and particularly to a method and an instrument requiring the use of only one hand to sever sutures.

Present suture removal kits include both a scissors and a forceps. The scissors normally provided are not normally honed to a sharp point since such suture removal kits are designed to be disposable and the extra cost of tooling and machining would be prohibitive. To employ such a kit, it is necessary to hold the scissors in one hand and the forceps in the other, lift the suture with the forceps, slide one blade of the scissors underneath the raised suture, cut the suture, and then remove the cut suture with the forceps. With this method, the surgeon must rely on a nurse or other assistant to immobilize the sutured area or risk gouging the patient if the patient should move. Since it is more desirable for the physician himself to control the patient with one hand and to flex or otherwise manipulate the sutured area for access, attempts have been made to employ a very sharply pointed scissors and eliminate the use of the forceps from the procedure. However, this necessitates an extreme risk of patient injury in approaching the sutured area with a sharply pointed scissors, lodging the point of one of the scissors blades underneath the suture, pushing the pointed end of the scissors forward without impaling the sutured surface, and then closing the scissors blades.

Neither of these methods is at all satisfactory where it is necessary to remove sutures in delicate or close quarters, such as inside of a nostril, in the area of the eye, behind the ear, and the like. In such areas there is simply not sufficient room to utilize both a forceps and scissors. Furthermore, it is often impossible to see the area being worked on when two hands, a forceps, and a scissors are being employed. This results in the distinct possibility of inadvertantly puncturing the sutured surface. In addition, such procedures require an extended period of time to remove sutures, during which time the patient is frequently extremely uncomfortable due to the necessity of providing sufficient access to the sutured area.

The suture removal method and instrument of this invention provide an inexpensive instrument which is quick, safe, and easy to operate, even in delicate situations, and which may be made disposable. This instrument and method afford almost total visibility of sutured surfaces in close quarters and allow the physician a free hand for controlling the patient.

SUMMARY OF THE INVENTION

A method of cutting sutures with an instrument operable with one hand is provided. The instrument comprises a thin, substantially flat blade having a sharp concave cutting edge and widening to a non-cutting, convex bearing edge. The cutting and bearing edges converge to a sharp point at a first blade end and diverging to a second blade end remote from the first end. The arc of the bearing edge is substantially equal to or less than the arc of the cutting edge. A handle is secured to the second end of the blade. An obtuse angle is formed between a line drawn parallel to the longitudinal axis of that portion of the handle which is connected to the blade and a line drawn tangent to the bearing edge at the point of the blade. The method comprises the steps of inserting the pointed end of the blade between a suture and the sutured surface with the sharpened edge in engagement with the suture and the non-cutting bearing edge in engagement with the sutured surface. The blade is then rotated to raise the suture from the sutured surface. The blade is then linearly advanced and further rotated to progressively increase the tension on the suture across the sharpened blade edge until the suture is severed.

DESCRIPTION OF THE DRAWINGS

The invention may best be understood when taken in conjunction with the following detailed description, wherein:

FIG. 1 is an elevational view of one embodiment of this invention;

FIG. 2 is a plan view taken along the line 2—2 of FIG. 1;

FIG. 3 is a cross-sectional elevational view of the blade taken along the line 3—3 of FIG. 1;

FIGS. 4, 5 and 6 are elevational views illustrating the manner in which a suture is severed employing the instrument of the embodiment shown in FIGS. 1–3; and, FIG. 7 is an elevational view illustrating the manner in which a severed suture is removed employing the instrument of the embodiment shown in FIGS. 1–3.

DETAILED DESCRIPTION

The suture removal instrument 10 of this invention includes a forceps 18 integrally molded at one end of a handle 12 and a curved blade 34 rigidly secured to the other end of the handle. Such an instrument thus allows a one-handed procedure since the physician is enabled, with one hand, to hold the instrument for cutting the suture and to then reverse the instrument with that same hand, as one would reverse a pencil, to employ the forceps to remove the severed suture. This procedure leaves the physician's other hand free to control the patient and/or the sutured area, such as in holding open a nostril or tensing an eyelid. The instrument is extremely simple to manufacture and may be made disposable. Furthermore, this suture removal procedure is extremely fast and efficient, enabling a physician to remove as many as about 20 stitches in about 35 seconds.

In order to remove a stitch, the point 40 of the blade is inserted underneath the suture and the blade is then rotated so that the suture slides back onto the sharpened concave cutting edge 38. At the same time, the flatened convex bearing edge 36 of the blade rests on the sutured surface while the point is directed away from the patient. This rotation is continued until the tension on the suture across the cutting edge of the blade becomes sufficient to sever the suture. The instrument is then reversed in the same hand, as previously described, to bring the forceps into operation to remove the suture. With the point of the blade directed away from the patient, the cutting edge of the blade spaced from the patient by the width of the blade, and the bearing edge in contact with the sutured surface, an extremely safe precedure is provided. In addition, the positioning of the handle with respect to the blade, as will be described hereinafter, allows blade rotation without substantial pressure on the sutured surface, eliminates any sharp fulcrum which would be painful or dangerous during blade rotation, and provides an instrument and method which are extremely useful and safe in delicate surgery and in small cavities, such as in the nose.

More specifically, the suture removal instrument shown in FIGS. 1-3 includes an elongated cylindrical handle 12, composed of plastic or the like, having a hexagonal cross-section to assist the user in gripping the instrument. A forceps 18 is formed integrally with one end 14 of the handle. Each of the bowed forcep legs 22 and 24 have a flatened end 26 and 28 respectively. When the legs are pushed towards each other, the flatened ends 26 and 28 contact each other over an area, such as two square millimeters, to grasp the end of a suture. In addition, each of the legs 22 and 24 have a serrated distal end 30 to assist in grasping suture material.

A thin, substantially flat, curved blade 34, composed of stainless steel or the like, is secured in an aperture (not shown) in a second end 16 of the handle 12 by epoxy glue or the like. The blade 34 has a wedge-shaped medial cross-section forming a substantially flat, convex bearing edge or surface 36 and a sharpened, concave cutting edge 38. The curvature of the cutting and bearing edges may vary somewhat, depending upon the use for which the instrument is designed. In this embodiment of the invention, the radius of curvature of both the cutting and bearing edges is 11/16ths inches. These two edges converge to form a point 40 at the leading end of the blade and diverge toward the handle 12. The two primary side surfaces 42 and 44 extend from the bearing surface to two sharpened surfaces 46 and 48 which join at the cutting edge 38. As is shown in FIG. 6, an obtuse angle 66 is formed between a line 68 drawn parallel to the longitudinal axis of that portion of the handle 12 which is connected to the blade and a line 70 drawn tangent to the bearing edge at the point of the blade.

In the method of employing this suture removal instrument, as shown in FIGS. 4-6, the point 40 of the blade is initially inserted under a stitch 52 with the bearing edge 36 near the point resting on the sutured surface 54, as is shown in FIG. 4. The blade is then rotated, as indicated by the arrow 56, to direct the point away from the sutured surface. This causes the bearing edge 36 further removed from the point to rest upon the sutured surface and the stitch 52 to be raised away from the sutured surface and to slide rearwardly along the cutting edge 38 away from the point 40, as is shown in FIG. 5. Upon further rotation of the blade, as indicated by arrow 58, the stitch will come under increasing tension and will also tend to slide further along the cutting edge 38 away from the point 40, thus eventually causing the stitch to be severed, as is shown in FIG. 6. Simultaneously with either or both rotation steps, some linear advancement of the blade is likely to naturally occur.

After the suture is severed, the instrument 10 is reversed in the same hand to bring the forceps into operation. The forceps is employed to grasp and remove the cut suture, such as by grasping a suture knot 60 as is shown in FIG. 7 and then pulling.

It will be understood that various modifications and changes may be made to the apparatus and method shown and described herein, all within the scope of the invention. For example, various degrees of curvature may be employed in forming the bearing and cutting edges, resulting in slightly modified utilization of the instrument. In addition, the bearing surface and the cross-sectional dimensions of the blade may be varied in shape, all within the scope of this invention.

What is claimed is:

1. A method of cutting sutures with an instrument operable with one hand, wherein said instrument comprises a thin, substantially flat blade having a sharp concave cutting edge and widening to a non-cutting, convex bearing edge, said cutting and bearing edges converging to a sharp point at a first blade end and diverging to a second blade end remote from the first end with the arc of said bearing edge being substantially equal to or less than the arc of said cutting edge, and a handle secured to said second end of the blade, an obtuse angle being formed between a line drawn parallel to the longitudinal axis of that portion of the handle which is connected to the blade and a line drawn tangent to the bearing edge at the point of the blade, comprising the steps of:
   inserting the pointed end of the blade between a suture and the sutured surface with the sharpened edge in engagement with the suture and the non-cutting bearing edge in engagement with the sutured surface;
   rotating the blade to raise the suture from the sutured surface and to direct the blade point away from the sutured surface; and,
   linearly advancing and further rotating the blade to progressively increase the tension on the suture across the sharpened blade edge until the suture is severed.

2. A method of cutting sutures with an instrument operable with on hand, wherein said instrument comprises a thin, substantially flat blade having a sharp concave cutting edge and widening to a non-cutting, convex bearing edge, said cutting and bearing edges converging to a sharp point at a first blade end and diverging to a wedged-shaped transverse cross-sectional area of the blade at a second blade end remote from the first end with the arc of said bearing edge being substantially equal to or less than the arc of said cutting edge, and a handle secured to said second end of the blade, an obtuse angle being formed between a line drawn parallel to the longitudinal axis of that portion of the handle which is connected to the blade and a line drawn tangent to the bearing edge at the point of the blade, comprising the steps of:
   inserting the pointed end of the blade between a suture and the sutured surface with the sharpened edge in engagement with the suture and the non-cutting, bearing edge in engagement with the sutured surface;
   rotating the blade to raise the suture from the sutured surface and to direct the blade point away from the sutured surface; and,
   linearly advancing and further rotating the blade to progressively increase the tension on the suture across the blade edge until the suture is severed.

3. A method of cutting sutures with an instrument operable with one hand as defined in claim 2, further comprising the step of:
   maintaining the non-cutting bearing edge in engagement with the sutured surface during the rotation of the blade to raise the suture from the sutured surface.

4. A method of cutting sutures with an instrument operable with one hand as defined in claim 2, comprising the further step of:
   maintaining the non-cutting, bearing edge in engagement with the sutured surface during both rotating steps.

5. A method of cutting sutures with an instrument operable with one hand as defined in claim 2, wherein the step of:
   linearly advancing and further rotating the blade is simultaneous; to direct the blade point away from the sutured surface.

* * * * *